(12) United States Patent
Hopper

(10) Patent No.: US 6,320,938 B1
(45) Date of Patent: *Nov. 20, 2001

(54) METHOD OF X-RAY PROTECTION DURING DIAGNOSTIC CT IMAGING

(75) Inventor: Kenneth D. Hopper, Hummelstown, PA (US)

(73) Assignee: F & L Medical Products, Vandergrift, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/181,429

(22) Filed: Oct. 28, 1998

(51) Int. Cl.$^7$ .................................................. G21K 3/00
(52) U.S. Cl. ............................. 378/156; 378/159; 378/18; 250/515.1
(58) Field of Search ................... 378/4, 18, 20, 378/156, 159; 250/515.1, 506.1, 507.1

(56) References Cited

U.S. PATENT DOCUMENTS

| | | | | |
|---|---|---|---|---|
| 2,328,105 | * | 8/1943 | Strobino | 250/108 |
| 3,045,121 | | 7/1962 | Leguillon | 250/108 |
| 3,154,789 | | 11/1964 | Lewis, Jr. | 2/104 |
| 3,185,751 | * | 5/1965 | Sutton | 264/301 |
| 3,286,094 | | 11/1966 | Pretto | 250/108 |
| 3,310,053 | | 3/1967 | Greenwood | 128/577 |
| 3,569,713 | | 3/1971 | Via, Jr. | 250/108 |
| 3,805,081 | | 4/1974 | Barthel et al. | 250/512 |
| 3,832,564 | | 8/1974 | Hall et al. | 250/510 |
| 3,917,954 | | 11/1975 | Boge | 250/510 |
| 3,937,971 | | 2/1976 | Morrison et al. | 250/515 |
| 3,942,023 | | 3/1976 | Flaugnatti | 250/515 |
| 3,999,073 | | 12/1976 | Hounsfield et al. | 250/445 T |
| 4,024,405 | | 5/1977 | Szot | 250/516 |
| 4,053,781 | | 10/1977 | Hounsfield | 250/456 |
| 4,082,957 | | 4/1978 | Morlan | 250/482 |
| 4,171,483 | | 10/1979 | Finkenzeller et al. | 250/321 |
| 4,172,979 | | 10/1979 | Morrison | 250/505 |
| 4,220,867 | | 9/1980 | Bloch, Jr. | 250/516 |
| 4,221,971 | | 9/1980 | Burger | 250/505 |
| 4,223,229 | | 9/1980 | Persico et al. | 250/515 |
| 4,266,139 | | 5/1981 | Sportelli et al. | 250/515 |
| 4,286,167 | | 8/1981 | La Riviere | 250/510 |
| 4,288,695 | | 9/1981 | Walters et al. | 250/445 T |
| 4,359,642 | | 11/1982 | Heinz et al. | 378/150 |
| 4,392,239 | | 7/1983 | Wilkens | 378/146 |
| 4,411,263 | | 10/1983 | Cook | 128/132 R |

(List continued on next page.)

OTHER PUBLICATIONS

"F&L Attenuating Gloves: Fluoroscopic Protection and Touch Sensitivity", two pages, undated.

Kenneth D. Hopper, M.D., Steven H. King, M.S., Mark E. Lobell, M.D., Thomas R. TenHave, Ph.D., Jill S. Weaver, B.S.R.T., "The Breast: In–plane X–ray Protection during Diagnostic Thoracic CT–Shielding with Bismuth Radioprotective Garments", Radiology, Dec. 1997, vol. 205 pp. 853–858, published Nov. 15, 1997.

*Primary Examiner*—David P. Porta
*Assistant Examiner*—Jurie Yun
(74) *Attorney, Agent, or Firm*—Thomas Hooker, P.C.

(57) ABSTRACT

A shield is placed on a patient's body over a secondary organ adjacent a target organ. The shield is partially transparent to x-ray radiation. A CT scan of the target organ is conducted according to conventional protocols and technical parameters. No artifacts are formed in the diagnostic portion of the CT image and there is no degradation of the diagnostic portion of the CT image. A reduction of between about 40% and about 60% in the radiation dose of the secondary organ as compared to the same CT scan made without the shield is achieved.

18 Claims, 3 Drawing Sheets

U.S. PATENT DOCUMENTS

| | | | |
|---|---|---|---|
| 4,490,616 | 12/1984 | Cipollina et al. | 250/515.1 |
| 4,581,752 | 4/1986 | De Luca | 378/62 |
| 4,641,336 | 2/1987 | Gastrin | 378/156 |
| 4,653,473 | 3/1987 | Kempe | 128/1 R |
| 4,670,658 | 6/1987 | Meyers | 250/519.1 |
| 4,670,896 | 6/1987 | Klausz | 378/156 |
| 4,701,962 | 10/1987 | Simon | 2/15 |
| 4,745,916 | 5/1988 | Seber | 128/155 |
| 4,868,843 | 9/1989 | Nunan | 378/152 |
| 4,868,844 | 9/1989 | Nunan | 378/152 |
| 4,924,103 | 5/1990 | Stein et al. | 250/516.1 |
| 4,938,233 | 7/1990 | Orrison, Jr. | 128/849 |
| 5,001,354 | 3/1991 | Gould et al. | 250/516.1 |
| 5,015,865 | 5/1991 | Sayers | 250/516.1 |
| 5,016,292 | 5/1991 | Rademacher | 2/431 |
| 5,022,099 | 6/1991 | Walton | 2/410 |
| 5,038,047 | 8/1991 | Still | 250/516.1 |
| 5,045,708 | 9/1991 | Cooper | 250/519.1 |
| 5,048,541 | 9/1991 | Haneline | 128/876 |
| 5,056,128 | 10/1991 | Thompson | 378/156 |
| 5,059,807 | 10/1991 | Kersten et al. | 250/519.1 |
| 5,099,135 | 3/1992 | Gemmill | 250/516.1 |
| 5,140,710 | 8/1992 | Rademacher | 2/432 |
| 5,144,647 | 9/1992 | Kikuchi | 378/153 |
| 5,166,531 | 11/1992 | Huntzinger | 250/505.1 |
| 5,190,990 | 3/1993 | Eichmiller | 523/137 |
| 5,207,233 | 5/1993 | Barnes | 128/842 |
| 5,233,990 | 8/1993 | Barnea | 128/653.1 |
| 5,242,372 | 9/1993 | Carol | 600/1 |
| 5,247,182 | 9/1993 | Servant et al. | 250/516.1 |
| 5,274,851 | 1/1994 | Simpkins, Sr. et al. | 2/102 |
| 5,360,666 | 11/1994 | Eichmiller | 428/327 |
| 5,417,225 | 5/1995 | Rubenstein et al. | 128/849 |
| 5,419,342 | 5/1995 | Scott | 128/846 |
| 5,454,023 | 9/1995 | Asikainen | 378/156 |
| 5,487,394 | 1/1996 | Shiu et al. | 128/846 |
| 5,523,581 | 6/1996 | Cadwalader | 250/519.1 |
| 5,533,089 | 7/1996 | Mulhern | 378/150 |
| 5,548,125 | 8/1996 | Sandbank | 250/519.1 |
| 5,548,627 | 8/1996 | Swerdloff et al. | 378/4 |
| 5,550,383 | 8/1996 | Haskell | 250/519.1 |
| 5,559,853 | 9/1996 | Linders et al. | 378/159 |
| 5,568,533 * | 10/1996 | Kumazaki et al. | 378/156 |
| 5,578,359 | 11/1996 | Forbes et al. | 428/131 |
| 5,602,895 | 2/1997 | Fivez et al. | 378/98.4 |
| 5,604,784 * | 2/1997 | Widlicka et al. | 378/203 |
| 5,621,188 | 4/1997 | Lee et al. | 174/35 MS |
| 5,638,545 | 6/1997 | Rosner | 2/16 |
| 5,644,614 | 7/1997 | Toth et al. | 378/147 |
| 5,666,396 | 9/1997 | Linders et al. | 378/156 |
| 5,669,395 | 9/1997 | Thompson | 128/846 |
| 5,822,393 | 10/1998 | Popescu | 378/108 |
| 5,976,998 * | 11/1999 | Sander et al. | 442/365 |

\* cited by examiner

METHOD OF X-RAY PROTECTION DURING DIAGNOSTIC CT IMAGING

FIELD OF THE INVENTION

The invention relates to a method of obtaining a diagnostic image using computer tomography.

BACKGROUND OF THE INVENTION

Diagnostic computer tomography (CT) is used to obtain a diagnostic image of a patient's internal organs. A CT scanner forms the image using x-rays. The patient is placed in the CT scanner between an x-ray source and an x-ray sensor so that x-rays pass through the patient's body and are detected by the x-ray sensor which then generates output signals based on the x-rays. A computer receives the signals and processes the signals to form parts of an image. The computer assembles the partial images from the scan to generate a desired cross section image of the body, including the organ or organs targeted for diagnosis.

A diagnostic CT examination commonly targets a specific body organ for diagnosis. For example, a thoracic CT scan typically obtains an image of the lungs or heart. Other organs commonly targeted for CT scans include the brain, spine and pelvis. The CT scan should return to the doctor a readable diagnostic image of the target organ.

During a CT scan, an organ other than the target organ may be exposed to x-rays. X-rays pass through the entire cross section of the body, and the x-rays will pass through an organ adjacent the target organ. The adjacent, secondary organ is seldom the target of a diagnostic CT examination. The secondary organ is exposed to x-rays as an incidental by-product of the CT examination of the target organ.

An organ may be radiosensitive, that is, the organ may be susceptible to cancer induced by radiation (including x-rays). Common radiosensitive organs exposed to x-rays as an incidental by-product of a CT examination include the breasts, eyes, thyroid and scrotum.

Incidental exposure of a radiosensitive secondary organ to x-rays may increase the risk of cancer. For example, a thoracic CT examination typically exposes each breast to a radiation dose of 2.0–3.5 rads. Young women are especially sensitive to radiation-induced breast cancer. It is desirable to reduce incidental exposure of secondary organs to x-rays.

Thus, there is a need for an improved method of obtaining a diagnostic image using a CT scanner. The method should reduce x-ray exposure to a radiosensitive secondary organ during CT examination of a target organ. The method should not degrade the diagnostic portion of the image nor contain artifacts that extend into the diagnostic portion of the diagnostic image. The method should be usable with existing CT scanners and scanner protocols.

SUMMARY OF THE INVENTION

The present invention is directed to an improved method of obtaining a diagnostic image using a CT scanner. The improved method reduces x-ray exposure to a radiosensitive secondary organ during CT examination of a target organ. The improved method does not degrade the diagnostic portion of the image and does not generate artifacts extending into the diagnostic portion of the image. The improved method is usable with existing CT scanners and scanner protocols.

A method to obtain a diagnostic image with a CT scanner having features of the present invention includes the step of placing a shield on a patient's body over a secondary organ adjacent a target organ. The shield is partially transparent to x-ray radiation. A CT scan of the target organ is conducted according to conventional protocols and technical parameters. X-rays pass through the target organ, the shield and secondary organ. A sensor detects the x-rays and generates signals. A computer processes the signals to form an image. No artifacts are formed in the diagnostic portion of the image and there is no degradation of the diagnostic portion of the image. The shield reduces the radiation dose of the secondary organ about 40% to 60% as compared to the radiation dose received during the same CT scan made without the shield.

In a preferred version of the method, the shield is a thin layer of radioabsorbent material. The material overlies the secondary organ and absorbs some of the x-rays that otherwise would have passed through the secondary organ. The material is smoothed to eliminate folds or creases that may cause an artifact in the image. The material selectively protects the secondary organ without affecting the diagnostic image of the target organ.

Other objects and features of the invention will become apparent as the description proceeds, especially when taken in conjunction with the accompanying drawings illustrating the invention, of which there are three sheets and three embodiments.

DESCRIPTION OF THE PREFERRED EMBODIMENTS

Figure 1:
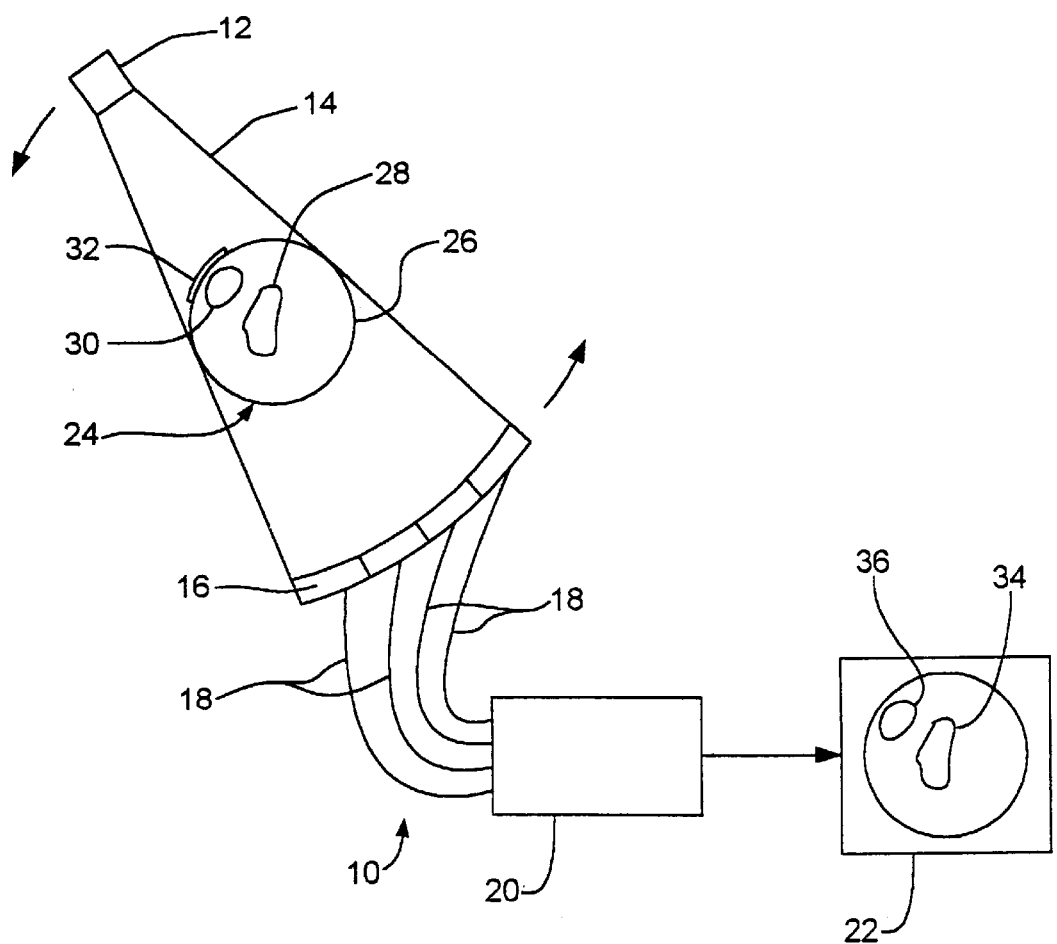
FIG. 1 schematically illustrates a diagnostic CT scan in accordance with the present invention.

FIG. 1 schematically illustrates a diagnostic CT scan in accordance with the present invention. A conventional CT scanner 10 forms a diagnostic image of a target organ. CT scanner 10 includes an x-ray source 12 that emits a diverging beam of x-rays 14. An x-ray sensor 16 is spaced from x-ray source 12 in the path of x-ray beam 14. X-ray sensor 16 detects the x-rays that strike the sensor and generates signals 18 based on the detected x-rays. A computer 20 receives signals 18 and processes the signals to form an image 22. CT scanner 10 may be a conventional CT scanner that scans individual sections of the body or a helical (spiral) CT scanner in which the patient is advanced at an even speed through the x-ray beam.

A patient 24 is placed in CT scanner 10 to obtain a diagnostic image of a target organ. Patient 24 is placed between x-ray source 12 and x-ray sensor 16 so that x-ray beam 14 passes through a cross-section 26 of the patient's body before striking x-ray sensor 16. Body cross-section 26 includes a target organ 28 that is the subject of the CT scan and an adjacent radiosensitive secondary organ 30 that is also within the x-ray beam.

A shield 32 is placed on the body of patient 24. Shield 32 overlies secondary organ 30. Shield 32 is partially transparent to x-rays. Shield 32 is located in-plane, that is, within the image 22 to be formed by CT scanner 10. Shield 32 preferably smoothly follows the body's surface. Folds or creases in shield 32 may present a sharp edge to the x-ray beam that may be seen as an undesirable artifact in image 22.

The CT scan is conducted according to conventional protocols and technical parameters. Both the target organ 28 and the secondary organ 30 are exposed to x-ray beam 14 by revolving x-ray source 12 and x-ray sensor 18 around patient 24 in a conventional manner. X-rays pass through body cross-section 26 and are detected by x-ray sensor to form image 22. X-rays pass through primary organ 28, secondary organ 30 and shield 32.

As x-ray source 12 revolves around patient 24, shield 32 comes between x-ray source 12 and secondary organ 30 (see FIG. 1). X-rays that would otherwise pass through secondary organ 30 first pass through shield 32. Shield 32 absorbs some of these x-rays, reducing the intensity of the x-rays reaching secondary organ 30 and reducing the radiation exposure of secondary organ 30 during the CT scan. Shield 32 reduces the radiation exposure of secondary organ 30 as compared to the same CT scan made without shield 32.

Shield 32 casts a shadow of reduced intensity x-rays on secondary organ 30 when shield 32 is between x-ray source 12 and secondary organ 30. Shield 32 is preferably sized so that during a portion of the revolution of x-ray source 12 around the patient, the entire secondary organ 30 falls within the reduced intensity x-ray shadow cast by shield 32. Increasing the size of shield 32 increases the period in which secondary organ 30 can remain in the reduced intensity x-ray shadow cast by shield 32 during the revolution of x-ray source 12. Preferably shield 32 is sized to reduce the radiation exposure of secondary organ 30 by between about 40% to 60% as compared to the same CT scan made without shield 32.

Computer 20 processes the signals 18 generated by x-ray sensor 16 in response to x-rays received by sensor 16, including the reduced intensity x-rays transmitted through shield 32 and secondary organ 30. Computer 20 generates an image 22 of body cross-section 26. Image 22 includes a readable diagnostic image portion 34 of target organ 28 and includes an image portion 36 of secondary organ 30. Any artifact in diagnostic image portion 34 caused by shield 32 is close to the skin's surface and does not extend into the diagnostic image portion 34. The diagnostic image portion is unaffected by shield 32.

Placing partially x-ray transparent shield 32 on a patient's body over a secondary organ 30 adjacent a target organ 28 during a diagnostic CT scan reduces x-ray exposure of the secondary organ between about 40% and 60%. The risk of cancer caused by x-ray exposure of the secondary organ is substantially reduced. The shield does not degrade the diagnostic image of the target organ. An image artifact generated by the shield occur near the skin and does not extend into the diagnostic image of the target organ.

Figure 2:
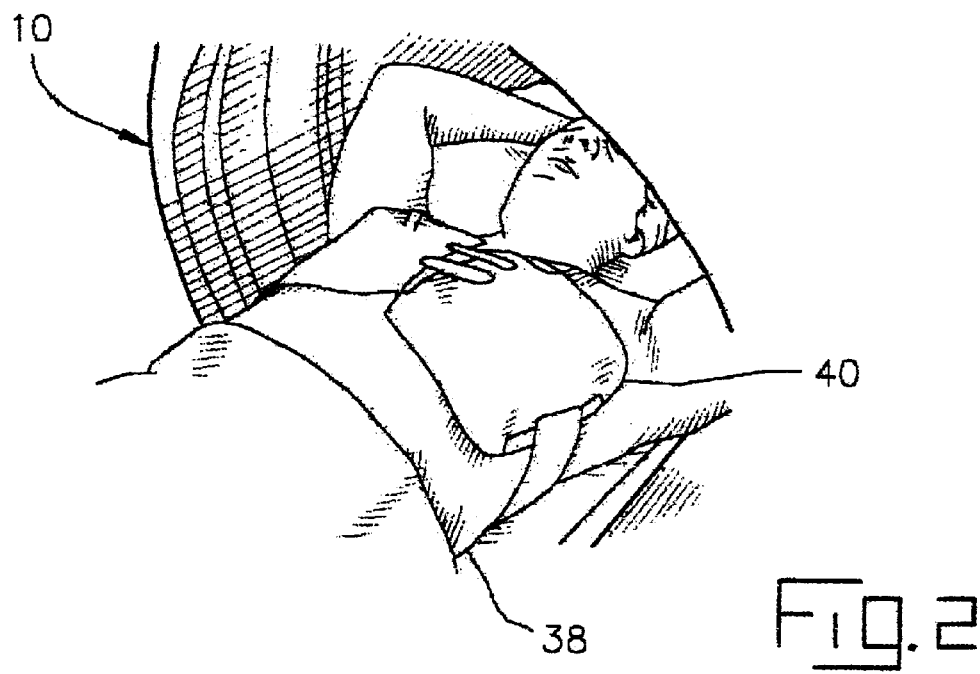
FIG. 2 illustrates a thoracic CT scan in accordance with the present invention.

FIG. 2 shows a patient 38 undergoing a thoracic CT scan in accordance with the present invention. A primary purpose of a thoracic CT scan is to provide a diagnostic image of the lungs or other target organs of the thorax. The breasts are a radiosensitive secondary organ adjacent the target organs. The breasts are exposed to the x-ray beam as an incidental by-product of a thoracic CT scan.

Prior to the thoracic CT scan, a shield 40 is placed over the breasts of patient 38. Shield 40 corresponds to shield 32 and fits smoothly over the breasts. Shield 40 is located within the image 22 to be formed by CT scanner 10. The thoracic CT scan is conducted according to conventional protocols and technical parameters. Both the target organ (lungs and/or organs of the thorax) and the secondary organ (breasts) are exposed to x-rays during the CT scan. Shield 42 reduces the x-ray exposure of the breasts by between about 40% to 60% as compared to the same CT scan made without shield 42. The image 22 formed by CT scanner 10 includes a readable diagnostic image portion 34 of the lungs or other organs of the thorax and includes an image portion 36 of the breasts. Any artifact in image 22 caused by shield 40 does not extend into the diagnostic portion of the image. The diagnostic image portion is unaffected by shield 40.

Figure 3:
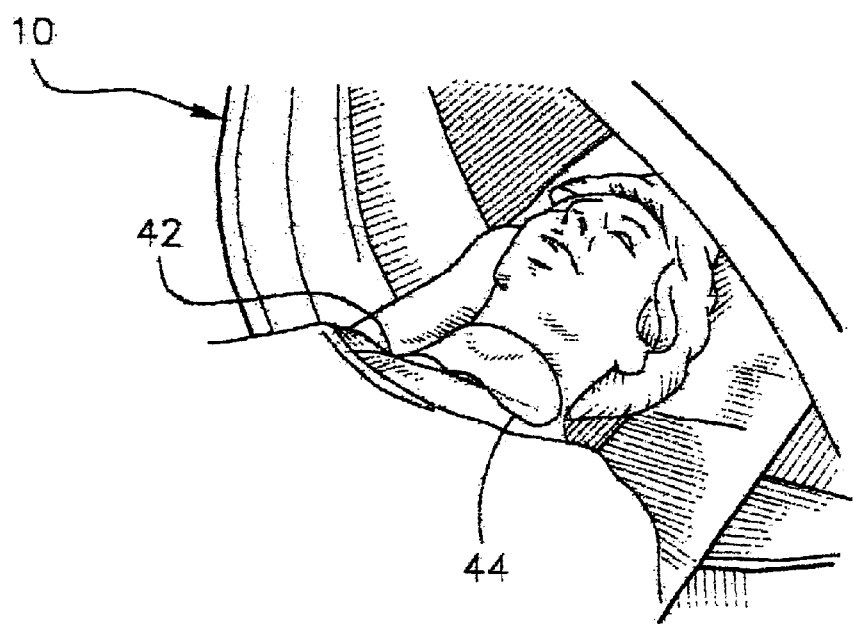
FIG. 3 illustrates a cervical CT scan in accordance with the present invention.

FIG. 3 shows a patient 42 undergoing a cervical CT scan in accordance with the present invention. A primary purpose of a cervical CT scan is to provide a diagnostic image of the spine in a patient's neck area. The thyroid is a radiosensitive organ adjacent the spine. The thyroid is exposed to the x-ray beam as an incidental by-product of a cervical CT scan.

Prior to the cervical CT scan, a shield 44 is placed over the thyroid of patient 42. Shield 44 is similar to shield 40 but is shaped to fit smoothly over the thyroid. Shield 44 is located within the image 22 to be formed by CT scanner 10. The cervical CT scan is conducted according to conventional protocols and technical parameters. Both the target organ (cervical spine) and the secondary organ (thyroid) are exposed to x-rays during the CT scan. Shield 44 reduces the x-ray exposure of the thyroid by between about 40% to 60% as compared to the same CT scan made without shield 44. The image 22 formed by CT scanner 10 includes a readable diagnostic image portion 34 of the cervical spine and includes an image portion 36 of the thyroid. Any artifact in image 22 caused by shield 44 does not extend into the diagnostic portion of the image. The diagnostic image portion is unaffected by shield 44.

Figure 4:
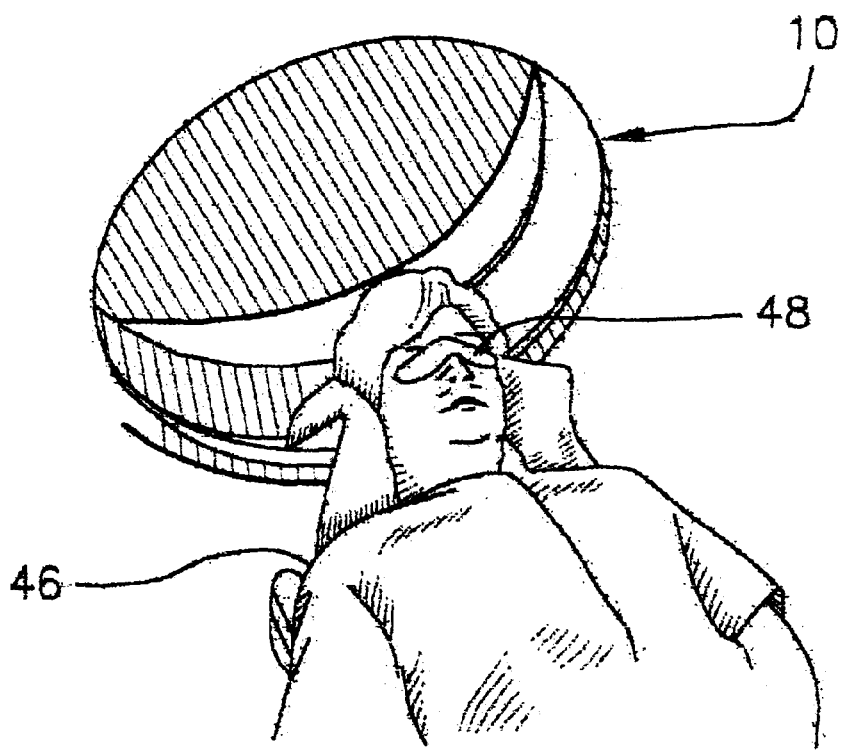
FIG. 4 illustrates an orbital CT scan in accordance with the present invention.

FIG. 4 shows a patient 46 undergoing an orbital CT scan in accordance with the present invention. A primary purpose of an orbital CT scan is to provide a diagnostic image of the brain. Each lens of the eye is a radiosensitive organ. Each lens is exposed to the x-ray beam as an incidental by-product of an orbital CT scan.

Prior to the orbital CT scan, a shield 48 is placed over the eyes of patient 46. Shield 48 is similar to shields 40 and 44 but is shaped to fit smoothly over the eyes. Shield 48 is located within the image 22 to be formed by CT scanner 10. The cervical CT scan is conducted according to conventional protocols and technical parameters. Both the target organ (brain) and the secondary organ (each lens) are exposed to x-rays during the CT scan. Shield 48 reduces the x-ray exposure of the lenses of the eyes by about 40% as compared to the same CT scan made without shield 48. The image 22 formed by CT scanner 10 includes a readable diagnostic image portion 34 of the brain and includes an image portion 36 of the lenses of the eyes. Any artifact in image portion 36 caused by shield 48 does not extend into the diagnostic image portion 34. The diagnostic image portion is unaffected by shield 48.

In another embodiment of the present invention (not shown), a shield is placed over a patient's scrotum to protect the testes (a radiosensitive organ) during a pelvic CT examination. The shield reduces the x-ray exposure of the testes by about half (51%) as compared to the same CT scan made without the shield. The diagnostic portion of the CT image is not affected by the shield.

Shields 32, 40, 44 and 48 are preferably formed from a thin layer of radioabsorbent material. The material should be elastic and moldable to the body surface so that folds and creases in the material may be smoothed out when the shield is applied onto the patient's body. The thickness of the material may vary, depending on the absorption of x-rays desired and the elasticity needed to have the shield smoothly overlie the secondary organ. Shields that reduce x-ray exposure of the secondary organ between about 40% to 60% during a CT scan are preferred.

A preferred radioabsorbent material is bismuth radioprotective latex, available from F&L Medical Products, Vandergrift, Pennsylvania. Bismuth radioprotective latex favorably absorbs x-rays and is sufficiently elastic and moldable to lie smoothly on a patient's body. Lead-impregnated latex, available from International Biomedical, Austin, Texas, may also be used.

Bismuth radioprotective latex materials that attenuate 14%, 28%, 42% and 56% of x-rays at 120 kV have been successfully used as shields. The attenuation level referred to in the preceding sentence is a physical property of the material related to the degree of transparency of the material to x-rays, and does not directly relate to the percent reduction in x-ray exposure of the secondary organ when the material is used as a shield in accordance with the present invention.

A shield may form a part of a form-fitting garment to be worn by the patient. For example, the radioabsorbent material may be sewn inside the cups of a brassiere. Care should be taken during fabrication to ensure there are no overlaps or gaps between seams. A protective brassiere lined with 56% bismuth radioprotective latex reduced radiation exposure of the breasts by about 57.1%. Some image artifacts were noted in superficial breast tissue, but the diagnostic image portions of the CT image were unaffected.

The shield overlays the secondary organ and effectively reduces the radiation exposure of the secondary organ during a CT scan. The shield comes between the x-ray source and the secondary organ when the x-ray source is closest to the secondary organ. Without the shield, the intensity of the x-ray beam striking the of secondary organ would then be at a maximum because of the relative nearness of the x-ray source and, particularly for a secondary organ located at or near the periphery of the body cross section, the substantial lack of body tissue between the secondary organ and the x-ray source. The shield reduces the intensity of the x-ray beam when the secondary organ needs protection most and would otherwise be exposed to a maximum intensity x-ray beam.

The shield also effectively protects the secondary organ from undesirable x-rays emitted by the x-ray source. Known x-ray sources emit x-rays that travel in an undesired direction (scatter) and x-rays that have an undesired frequency. These undesirable x-rays are readily absorbed by human tissue, and are generally absorbed by the patient in a relatively thin surface layer facing the x-ray source. Secondary organs typically are located near the skin and are susceptible to absorbing these undesirable x-rays when the x-ray source travels over the secondary organ. The shield absorbs undesirable x-rays that would otherwise be absorbed by the secondary organ.

It is not necessary that the shield be substantially larger than that needed to overlay the secondary organ itself. As the x-ray source revolves past the secondary organ, the distance between the x-ray source and the secondary organ increases. The intensity of the x-ray beam striking the secondary organ decreases with increased distance from the x-ray source. The x-ray beam must also pass through an increasingly thick layer of intervening body tissue before reaching the secondary organ. Absorption of the x-ray beam by the intervening tissue further decreases the intensity of the x-ray beam at the secondary organ. In the portion of a CT scan where the x-ray beam no longer passes through the shield before reaching the secondary organ, the increased x-ray source distance and intervening body tissue substantially reduce the intensity of x-rays at the secondary organ without the need of additional shielding.

The use of a shield partially transparent to x-rays to protect a secondary organ during a diagnostic CT scan in accordance with the present invention reduces x-ray exposure of the secondary organ between about 40% and 60%. The risk of cancer in the secondary organ is substantially reduced.

While I have illustrated and described preferred embodiments of my invention, it is understood that this is capable of modification, and I therefore do not wish to be limited to the precise details set forth, but desire to avail myself of such changes and alterations as fall within the purview of the following claims.

What I claim as my invention is:

1. A method of generating a diagnostic image of a cross section of a target patient organ located adjacent a radiosensitive secondary organ by a computed tomography scanner, the scanner having a revolvable x-ray source and x-ray sensor, said method comprising the steps of:

(a) placing the patient between the x-ray source and the x-ray sensor of the computed tomography scanner to scan a patient cross section including the target organ and the secondary organ;

(b) placing a shield partially transparent to x-rays over the secondary organ, the shield not extending around the entire cross section of the patient;

(c) revolving the x-ray source and the x-ray sensor around the patient, the shield located between the x-ray source and the secondary organ for less than an entire revolution of the x-ray source around the patient;

(d) transmitting x-rays emitted from the revolving x-ray source through the target organ, the secondary organ and the shield and to the sensor to scan the patient with the computed tomography scanner, the scanner configured to irradiate the cross section with an x-ray intensity;

(e) absorbing x-rays passing through the shield when the shield is between the secondary organ and the x-ray source to reduce the radiation dose received by the secondary organ from the scan by between 40% and 60% of the radiation dose that would have been received by the secondary organ from a like scan made with the same x-ray intensity but without the shield; and (f) processing signals generated by the sensor in response to the x-rays received by the x-ray sensor during the scan, including the x-rays transmitted through the shield and the secondary organ, to generate a readable diagnostic image of the target organ.

2. The method of claim 1 comprising the step of:

(g) placing the shield on the patient and over the secondary organ.

3. The method of claim 2 comprising the step of:

(h) conforming the shape of the shield to the shape of the body of the patient over the secondary organ.

4. The method of claim 1 comprising the step of:

(g) positioning a radioabsorbent bismuth latex shield over the secondary organ only.

5. The method of claim 1 comprising the step of:

(g) placing a radioabsorbent bismuth latex shield that attenuates between 14% and 56% of x-rays at 120 kV on the patient over the secondary organ.

6. The method of claim 1 comprising the step of:
(g) attaching the shield to a form-fitting garment and placing the form-fitting garment on the patient.

7. The method of claim 6 comprising the step of:
(h) attaching the shield to a brassiere and fitting the brassiere over the breasts of the patient.

8. The method of claim 1 comprising the step of:
(g) shadowing the entire secondary organ with the shield from the x-rays emitted by the x-ray source when the shield is between the x-ray source and the secondary organ.

9. The method of claim 1 comprising the step of:
(g) intersecting the path of some, but not all, of the emitted x-rays radiating the cross section of the patient with the shield when the shield is located between the x-ray source and the secondary organ.

10. A method for reducing the x-ray dose of a radiosensitive secondary organ of a patient from radiation emitted during a diagnostic computed tomography scan of an adjacent target organ by a computed tomography scanner comprising the steps of:
(a) positioning the body of a patient between an x-ray source and an x-ray sensor of the computed tomography scanner;
(b) emitting a beam of x-rays from the x-ray source through a cross section of the body including the target organ and the radiosensitive secondary organ and to the x-ray sensor, the x-ray beam having an intensity where the beam intersects the cross section of the body;
(c) moving the x-ray source and sensor along a path extending around the body cross section so that both the target organ and the secondary organ are radiated by the x-ray beam, the path having a portion wherein the x-ray source is closest to the secondary organ, said x-ray beam comprising a first beam portion radiating the secondary organ and a second beam portion, said first beam portion less than the entire x-ray beam;
(d) reducing the intensity of the first beam portion and not reducing the intensity of the second beam portion when the x-ray source is along said closest path portion, the reduction in intensity of the first beam portion sufficient to appreciably reduce the x-ray dose received by the secondary organ from the scan compared to an x-ray dose received by the secondary organ from a like computer tomography scan made without such reduction of intensity; and
(e) processing signals generated by the x-ray sensor in response to x-rays received by the x-ray sensor, including the reduced intensity x-rays transmitted through the secondary organ, to generate a readable diagnostic image of the target organ.

11. The method of claim 10 comprising the step of:
(f) placing an x-ray shield on the body of the patient over the secondary organ and partially absorbing x-rays in the shield before the x-rays radiate the secondary organ.

12. The method of claim 11 comprising the step of:
(g) partially absorbing undesirable scatter x-rays emitted by the x-ray source in the shield before the undesirable x-rays radiate the secondary organ.

13. The method of claim 10 comprising the step of:
(f) reducing the intensity of x-rays emitted toward the secondary organ whereby the radiation dose of the secondary organ is reduced by between 40% and 60%.

14. The method of claim 13 comprising the step of:
(g) placing a shield partially transparent to x-rays over the secondary organ without appreciably shielding the target organ; and
(h) transmitting x-rays through the shield to the secondary organ, the shield shadowing the entire secondary organ with reduced intensity x-rays.

15. The method of claim 10 comprising the step of:
(f) not reducing the intensity of the said first beam portion when the x-ray source is not along said closest path portion.

16. The method of claim 10 comprising the step of:
(f) locating a shield partially transparent to x-rays between the x-ray source and the secondary organ only to partially absorb x-rays emitted toward the secondary organ.

17. The method of claim 16 comprising the step of:
(g) placing the shield on the body of the patient directly over the secondary organ.

18. The method of claim 10 comprising the step of:
(f) absorbing x-rays emitted from the x-ray source toward the secondary organ before the x-rays radiate the body cross section.

* * * * *